US00PP24828P3

(12) United States Plant Patent
Bédard

(10) Patent No.: US PP24,828 P3
(45) Date of Patent: Sep. 2, 2014

(54) SHRUB ROSE PLANT NAMED 'WEKRUNEFLO'

(50) Latin Name: *Rosa hybrida*
Varietal Denomination: WEKruneflo

(71) Applicant: Early Morning LLC, Pomona, CA (US)

(72) Inventor: Christian Bédard, Brea, CA (US)

(73) Assignee: Early Morning LLC, Pomona, CA (US)

( * ) Notice: Subject to any disclaimer, the term of this patent is extended or adjusted under 35 U.S.C. 154(b) by 124 days.

(21) Appl. No.: 13/694,481

(22) Filed: Dec. 5, 2012

(65) Prior Publication Data

US 2014/0157462 P1 Jun. 5, 2014

(51) Int. Cl.
*A01H 5/00* (2006.01)

(52) U.S. Cl.
USPC ..... Plt./107; Plt./101; Plt./102; Plt./106

(58) Field of Classification Search
USPC ..... Plt./101, 102, 106, 107
See application file for complete search history.

(56) References Cited

U.S. PATENT DOCUMENTS

PP15,066 P2 8/2004 Carruth

*Primary Examiner* — Susan McCormick Ewoldt
(74) *Attorney, Agent, or Firm* — McKee, Voorhees & Sease

(57) ABSTRACT

A new variety of Shrub rose suitable for garden decoration, having flowers of orangey pink with a yellow eye coloration.

1 Drawing Sheet

Classification: The present invention relates to a new *Rosa hybrida* plant.

Variety denomination: The new plant has the varietal denomination 'WEKruneflo'.

BACKGROUND OF THE INVENTION

This invention relates to a new and distinct variety of Shrub Rose. It has as its seed parent the variety known as 'WEKsactrumi' (U.S. Plant Pat. No. 15,066) and a non-disseminated seedling of my creation as its pollen parent with the following genetic origin (Neon Cowboy×Flower Carpet).

SUMMARY OF THE INVENTION

Among the features which distinguish the new variety from other presently available and commercial rose cultivars known to the inventor are the following combinations of characteristics: its large clusters of orangey pink with a yellow eye flower coloration, its excellent degree of resistance to powdery mildew, downy mildew and rust, its very abundant bloom and its even bushy rounded moderately spreading growing habit. The plant has a bushy rounded moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKruneflo' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKsactrumi' by the following combination of characteristics: whereas 'WEKruneflo' bears medium sized flowers (about 7.2 to about 9.3 cm. in diameter) of orangey pink with a yellow eye coloration, 'WEKsactrumi' bears significantly smaller flowers (about 4 to about 5 cm. in diameter) of cherry red coloration. The new variety is classified as a Shrub rose with a bushy rounded moderately spreading medium height growing habit (about 100 to about 125 cm. in height), whereas the seed parent is classified as a Miniature rose with a bushy moderately spreading significantly shorter growing habit (about 60 to about 77 cm. in height).

The new variety may be distinguished from its pollen parent, a non-disseminated seedling of my creation by the following combination of characteristics: whereas 'WEKruneflo' bears semi-double flowers (about 6 to 8 petals) of orangey pink with a yellow eye coloration, the non-disseminated seedling bears double flowers of light pink with a white 'eye' coloration with significantly heavier petalage (about 17 to 25 petals). The new variety has a bushy rounded moderately spreading medium height growing habit (about 100 to about 125 cm. in height), whereas the pollen parent has a bushy spreading significantly shorter growing habit (about 56 to about 75 cm. in height).

COMPARISON WITH THE CLOSEST COMMERCIALLY AVAILABLE CULTIVAR

The new variety may be distinguished from its closest commercially available cultivar, 'MEIzmea' (U.S. Plant Pat. No. 20,175) by the following combination of characteristics: whereas 'WEKruneflo' bears semi-double flowers (about 6 to 8 petals) of orangey pink with a yellow eye coloration, 'MEIzmea' bears single flowers of bright red with a light of pink center coloration with significantly lesser petalage (commonly approximately 5 petals). The new variety bears medium size flowers (about 7.2 to about 9.3 cm. in diameter), whereas the closest commercially available cultivar bears significantly smaller flowers (approximately 2.2 cm. in diameter on average).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, usually in clusters of 7 to 17 per stem. Flowers may be borne in regular rounded clusters on strong somewhat short to medium length stems (about 26 to about 65 cm.). Outdoors, the plant blooms very abundantly and nearly continuously during the growing season. The flowers have a light tea fragrance.

BUD

The peduncle is about 2.4 to about 3.9 cm. in length, of slender caliper (about 0.2 to about 0.3 cm. in diameter), and usually erect to somewhat stiff. It is moderately rough, with some stipitate glands and very few hairs. Peduncle color is between 144A and 143B often heavily suffused, especially on the side exposed to the sun, with between 187A and 187B.

Before the calyx breaks, the bud is about 0.9 to about 1.3 cm. in diameter at the widest point, about 1.3 to about 1.6 cm. in length, and pointed to somewhat ovoid in shape. The surface of the bud bears about 5 foliaceous appendages, usually with slender foliaceous parts extending beyond the tip of the bud about ½ or more of its length. Bud color is between 146A and 146B sometimes lightly suffused, especially on the side exposed to the sun, with between 187A and 187B.

The sepals are about 2.8 to about 3.4 cm. in length and about 0.5 to about 0.7 cm. in width at the widest point. The outer surface color of the sepal is between 146A and 146B sometimes lightly suffused, especially on the side exposed to the sun, with between 187A and 187B. The outer surface of the sepal is smooth and bears about 2 foliaceous appendages with very few stipitate glands and hairs. The inner surface color of the sepal is near 139C. The inner surface of the sepal is covered with fine wooly tomentum; sepal margins are lined with some stipitate glands and hairs.

The receptacle of the flower is somewhat short in length (about 0.4 to about 0.5 cm.) and moderately thin in caliper (about 0.4 to about 0.6 cm. in diameter). The receptacle is urn-shaped in form. Its surface is smooth with somewhat thin fleshy walls. The receptacle color is between 146A and 146B.

As the petals open (after the calyx breaks), the bud is about 1.1 to about 1.3 cm. in diameter at the widest point, about 1.5 to about 2.1 cm. in length, and pointed to somewhat ovoid in form. The color of the under surfaces of the newly opened petals is near 54C, gradually suffusing to the edge of the petal with between 54B and 53B. At the point where the petal attaches, there is a large zone of between 1C and 4C. The color of the upper surfaces of the newly opened petals is near 45B sometimes moderately suffused with near 46A. At the point where the petal attaches, there is a large zone of between 154C and 154D.

BLOOM

When fully open, the bloom ranges from about 7.2 to about 9.3 cm. in diameter. Petalage is semi-double with about 6 to 8 petals and about 1 to 3 petaloids irregularly arranged. When partially open, the bloom form is moderately cupped to somewhat ovoid, and the petals are moderately cupped to undulated with undulated petal edges somewhat reflexed outward. When fully open, the bloom form is more cupped, and the petals are loosely cupped to undulated with undulated petal edges moderately reflexed outward.

PETALS

The substance of the petals is slightly heavy and of medium thickness, with upper surfaces moderately satiny and under surfaces somewhat shiny. The petals are about 2.9 to about 4.0 cm. in length and about 3.5 to 4.5 cm. in width at the widest point. Petal margins are entire.

The outer petals are broadly obovate to somewhat rounded in shape with rounded to moderately retuse apices.

The inner petals are broadly obovate in shape with rounded to moderately retuse apices.

Petaloids are about 0.1 to about 2.3 cm. in length and about 0.5 to about 1.5 cm. in width at the widest point. Petaloids are irregularly shaped nearly oblanceolate to obovate with somewhat obtuse apices.

NEWLY OPENED FLOWER

The under surface color of the outer, intermediate and inner petals is between 18A and 23C gradually suffusing toward the petal edge with between 54C and 52D sometimes blushed with between 60C and 59C. At the point where the petal attaches, there is a moderately large zone of between 154C and 154D. The upper surface color of the outer, intermediate and inner petals is between 46C and 52B sometimes moderately blushed with between 46B and 46A. At the point where the petal attaches, there is large zone of between 1D and 1B.

The under and upper surface colors of the petaloids are similar in coloration to the upper and under surfaces of the inner petals.

The general tonality of the newly opened flower is between 46C and 52B sometimes moderately blushed with between 46B and 46A.

THREE-DAY-OLD FLOWER

The under surface color of the outer, intermediate and inner petals is between 56A and 49C sometimes lightly blushed with between 61A and 61B. At the point where the petal attaches, there is a large zone of between 154D and 2D. The upper surface color of the outer, intermediate and inner petals is between 58B and 52B sometimes moderately blushed with between 53B and 53C. At the point where the petal attaches, there is a large zone of between 154C and 154D.

The under and upper surface colors of the petaloids are similar in coloration to the upper and under surfaces of the inner petals.

The general tonality of the three-day-old flower is between 58B and 52B sometimes moderately blushed with between 53B and 53C.

On the spent bloom, the petals usually drop off cleanly and are not particularly affected by cold, hot, wet, or dry weather.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 127) and are arranged regularly about the pistils; a few are mixed with petaloids. The filaments are of somewhat long length (about 0.5 to about 1.3 cm.) most with anthers. Filaments are between 3A and 5B in color. The anthers are somewhat small for the class and all open approximately at the same time. Anther color when immature is near 22A on the external part and near 13D on the internal part. Anther color at maturity is near 165A on the external part and near 200C on the internal part. Pollen is abundant and between 18D and 13D in color.

FEMALE REPRODUCTIVE ORGANS

Pistils vary in number (average about 44). The styles are somewhat even, moderately long in length (about 0.2 to about 0.7 cm.), somewhat heavy in caliper and bunched. Stigma color is near 13B. Style color is near 150D. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 6.0 to about 17.0 cm. in length and about 4.5 to about 10.0 cm. in width at the widest point, leathery to somewhat crisp in texture, and glossy in finish on the upper side and semi-glossy in finish on the underside. The leaves have a pinnate venation pattern. The terminal leaflets are about 2.8 to about 6.0 cm. in length and about 2.3 to about 3.0 cm. in width at the widest point, shaped oval to ovate with somewhat acute to acuminate apices and moderately rounded to somewhat acute bases. Their margins are usually simply serrate.

The upper surface color of the mature leaf is between 147A and 137A. The under surface color of the mature leaf is between 147B and 137C. The upper and under colors of the leaf veins on the mature leaf are similar in coloration to the upper and under surfaces colors of the mature leaf. The upper surface color of the young leaf is between 137B and 141A often moderately suffused with between 187A and 187B on the leaf margins. The under surface color of the young leaf is between 146B and 137C often moderately suffused, especially on the leaf margins and the midrib, with between 187B and 183B. The under and upper colors of the leaf veins on the young leaf are similar in coloration to the upper and under surfaces colors of the young leaf.

The rachis is somewhat light to average in caliper and smooth. The upper side is shallowly grooved with few stipitate glands on the edges of the grooves. The underside of the rachis is smooth. The rachis color is near 146C on the underside and near 138A on the upper side often moderately suffused, especially on the young leaf, with near 187B.

The stipules are about 1.5 to about 3.5 cm. in length and wide (about 0.4 to about 1.2 cm. in width) with long straight points that usually turn out at an angle of more than 45 degrees. The under and upper surface color of the stipule is between 137B and 138A often moderately suffused, especially on the young leaf, with between 187A and 187B.

The petiole is somewhat light to average in caliper and smooth. The upper side is shallowly grooved with few stipitate glands on the edges of the grooves. The underside of the petiole is smooth. The petiole is about 0.9 to about 2.3 cm. in length and about 0.1 to 0.25 cm. in width at the widest point. The petiole color is near 146C on the underside and near 138A on the upper side often moderately suffused, especially on the young leaf, with near 187B.

The plant displays an excellent degree of resistance to powdery mildew, downy mildew and rust and an average degree of resistance to black spot as compared to other commercial varieties grown under comparable conditions in Pomona, Calif. The plant's winter hardiness and drought/heat tolerance are yet to be determined.

GROWTH

The plant has a bushy rounded moderately spreading medium height growing habit (about 100 to about 125 cm. in height and about 125 to about 225 cm. spread at the widest point), with full branching. It displays vigorous growth and the canes are of somewhat heavy caliper for the class (about 1.2 to about 1.8 cm. in diameter at the widest point).

The color of the major stems is between 146B and 146C. They bear few large prickles that are about 0.5 to about 1.0 cm. in length. The large prickles are almost straight and hooked slightly downward with a moderately long broad oval base; prickle color is between 166A and 165A. The major stem bears few small prickles of similar shape and coloration.

The color of the branches is between 146B and 138A sometimes lightly suffused with between 187B and 183A. They bear few large prickles which are of similar size and shape to the large prickles on the major stems; prickle color is between 165A and 166A. The branches bear few small prickles of similar shape and coloration.

The color of the new shoots is between 146B and 138A sometimes lightly suffused with between 187B and 183A. They bear some large prickles which are of similar size and shape to the large prickles on the major stems; prickle color is between 146C and 147C often lightly suffused with between 187B and 187C. The shoots bear few small prickles of similar shape and coloration.

I claim:

1. A new and distinct Shrub rose plant of the variety substantially as described and illustrated herein.

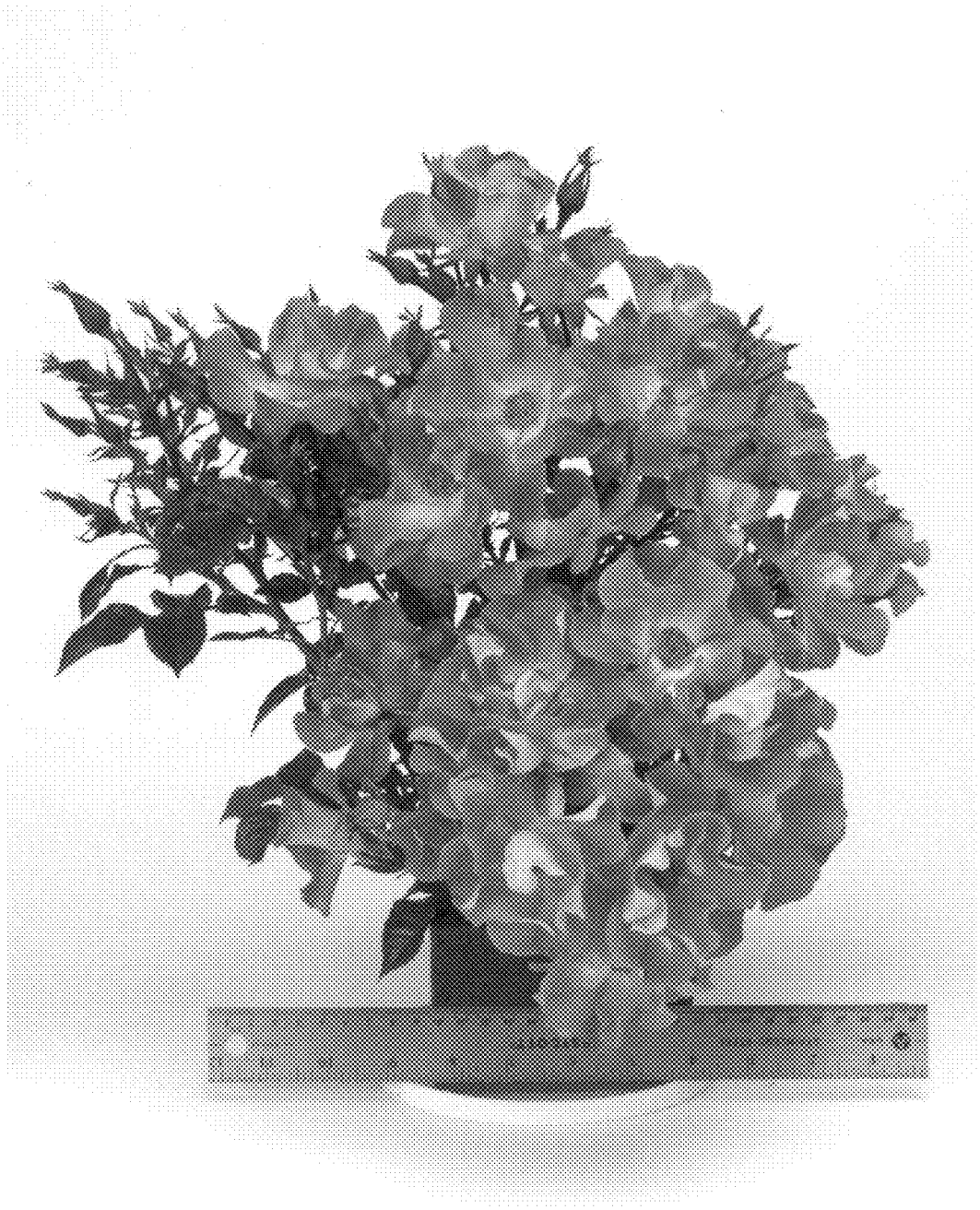

* * * * *